United States Patent
Anzai et al.

(10) Patent No.: US 10,022,478 B2
(45) Date of Patent: Jul. 17, 2018

(54) MEDICAL DEVICE

(71) Applicant: TERUMO KABUSHIKI KAISHA, Shibuya-ku, Tokyo (JP)

(72) Inventors: Takao Anzai, Kanagawa (JP); Kaori Nishida, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 2 days.

(21) Appl. No.: 15/193,888

(22) Filed: Jun. 27, 2016

(65) Prior Publication Data

US 2016/0303296 A1 Oct. 20, 2016

Related U.S. Application Data

(63) Continuation of application No. PCT/JP2014/083755, filed on Dec. 19, 2014.

(30) Foreign Application Priority Data

Dec. 27, 2013 (JP) .................. 2013-270963

(51) Int. Cl.
   *A61L 33/00* (2006.01)
   *A61L 33/06* (2006.01)
   (Continued)

(52) U.S. Cl.
   CPC ......... *A61L 33/0035* (2013.01); *A61L 31/048* (2013.01); *A61L 31/16* (2013.01);
   (Continued)

(58) Field of Classification Search
   CPC .... A61L 31/048; A61L 31/16; A61L 33/0023; A61L 33/0035; A61L 33/064;
   (Continued)

(56) References Cited

U.S. PATENT DOCUMENTS 5,756,785 A 5/1998 O'Lenick, Jr.
2003/0028073 A1 2/2003 Mochizuki et al.
(Continued)

FOREIGN PATENT DOCUMENTS

| JP | 04-152952 A | 5/1992 |
| JP | 2003-111836 A | 4/2003 |
| JP | 2007-130194 A | 5/2007 |
| JP | 2008-274151 A | 11/2008 |

(Continued)

OTHER PUBLICATIONS

International Search Report (PCT/ISA/210) dated Mar. 24, 2015, by the Japanese Patent Office as the International Searching Authority for International Application No. PCT/JP2014/083755.

Written Opinion (PCT/ISA/237) dated Mar. 24, 2015, by the Japanese Patent Office as the International Searching Authority for International Application No. PCT/JP2014/083755.
Extended Search Report issued by the European Patent Office in corresponding European Patent Application No. 14875327.0 dated Jul. 26, 2017 (5 pages).

*Primary Examiner* — Matthew P Coughlin
*Assistant Examiner* — Thurman M Wheeler
(74) *Attorney, Agent, or Firm* — Buchanan Ingersoll & Rooney PC

(57) ABSTRACT

A medical device is provided including a base member and a coating layer containing an antithrombogenic material and covering a surface of the base member. The antithrombogenic material contains a copolymer having a repeating unit (A) represented by the following formula (1):

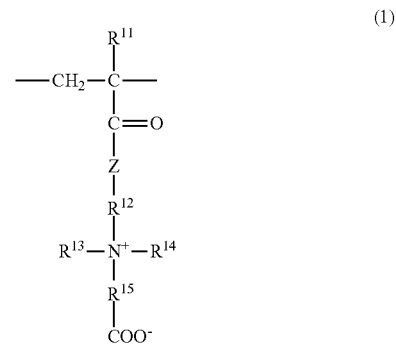

(1)

wherein $R^{11}$ is a hydrogen atom or a methyl group, Z is an oxygen atom or —NH—, $R^{12}$ is a $C_{1-6}$ alkylene group, $R^{13}$ and $R^{14}$ are each independently a $C_{1-4}$ alkyl group, and $R^{15}$ is a $C_{1-2}$ alkylene group, and a repeating unit (B) represented by the following formula (2):

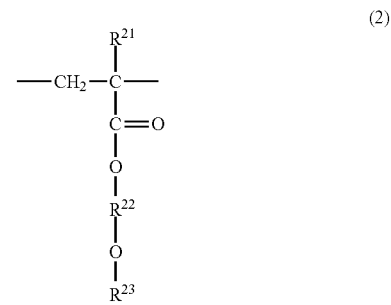

(2)

wherein $R^{21}$ is a hydrogen atom or a methyl group, $R^{22}$ is a $C_{1-6}$ alkylene group, and $R^{23}$ is a $C_{1-4}$ alkyl group. The repeating unit (A) is contained in a proportion of 1 to 7 mol % based on all the structural units of the copolymer.

21 Claims, 6 Drawing Sheets

(5 of 6 Drawing Sheet(s) Filed in Color)

(51) Int. Cl.
*A61L 31/16* (2006.01)
*A61L 31/04* (2006.01)

(52) U.S. Cl.
CPC ......... *A61L 33/0023* (2013.01); *A61L 33/064* (2013.01); *A61L 33/068* (2013.01); *A61L 2300/42* (2013.01); *A61L 2300/604* (2013.01); *A61L 2300/606* (2013.01); *A61L 2420/02* (2013.01)

(58) Field of Classification Search
CPC ............... A61L 33/068; A61L 2300/42; A61L 2300/604; A61L 2300/606; A61L 2420/02
See application file for complete search history.

(56) References Cited

U.S. PATENT DOCUMENTS

| | | |
|---|---|---|
| 2008/0262181 A1 | 10/2008 | Kitano et al. |
| 2010/0145286 A1 | 6/2010 | Zhang et al. |
| 2010/0176048 A1* | 7/2010 | Sakaguchi .............. A61L 31/16 210/321.62 |

FOREIGN PATENT DOCUMENTS

| | | |
|---|---|---|
| JP | 2010-057745 A | 3/2010 |
| WO | WO 2005/113620 A1 | 12/2005 |

* cited by examiner

MEDICAL DEVICE

CROSS-REFERENCES TO RELATED APPLICATIONS

This application is a continuation of International Application No. PCT/JP2014/083755 filed on Dec. 19, 2014, and claims priority to Japanese Application No. 2013-270963 filed on Dec. 27, 2013, the entire content of which is incorporated herein by reference.

TECHNICAL FIELD

The present disclosure relates to a medical device. For example, the present disclosure relates to a medical device having excellent antithrombogenicity.

BACKGROUND DISCUSSION

In recent years, medical materials utilizing various polymer materials have been studied, and they are expected to be used for membranes for artificial kidneys, membranes for plasma skimming, catheters, stents, membranes for artificial lungs, artificial blood vessels, anti-adhesion membranes, artificial skins, and the like. In these materials, a synthetic polymer material, which is a xenobiotic substance, is used in contact with a biological tissue or a body fluid such as blood. Therefore, it can be desirable for such a medical material to be biocompatible. The desired biocompatibility for a medical material can vary depending on its purpose and usage. It can be desirable for a medical material used as a material that contacts blood to have characteristics of inhibiting the blood coagulation system, inhibiting the adhesion/activation of platelets, and inhibiting the activation of the complement system (antithrombogenicity).

A medical device can be made antithrombogenic by a method in which the base member forming the medical device is covered with an antithrombogenic material, or a method in which an antithrombogenic material is fixed to the surface of the base member.

For example, JP-A-4-152952 discloses a membrane for an artificial organ or a medical device, having on the surface thereof a synthetic polymer that simultaneously satisfies biocompatibilities of inhibiting the adhesion/activation of platelets, an inhibitory effect on the activation of the complement system, and affinity with in-vivo tissues. In addition, U.S. Patent Application Publication No. 2008/0262181 (corresponding to International Publication No. WO 2005/113620) discloses a biocompatible material containing a homopolymer or copolymer that has reduced interaction with biological components such as proteins and blood cells and is highly biocompatible.

SUMMARY

The membrane disclosed in JP-A-4-152952 shows excellent results in terms of inhibiting the adhesion/activation of platelets. In addition, according to U.S. Patent Application Publication No. 2008/0262181 (corresponding to International Publication No. WO 2005/113620), the provided biocompatible material is excellent in terms of being capable of inhibiting the adsorption of proteins.

However, when a medical device has steps on the surface thereof that contacts blood, the blood flow is impaired at the steps, resulting in a tendency that thrombus formation is likely to occur around the steps. For example, in a blood flow circuit of a medical device, the blood flow is likely to be impaired around a constricted portion such as the joint of tubes used for the medical device, whereby thrombus formation is relatively likely to occur. Then, under such severe conditions relatively prone to thrombus formation, the materials according to the disclosures in JP-A-4-152952 and U.S. Patent Application Publication No. 2008/0262181 (corresponding to International Publication No. WO 2005/113620) have been sometimes insufficient in terms of antithrombogenicity.

Thus, the present disclosure has been accomplished against the above background, and an exemplary aspect thereof is to provide a medical device having excellent antithrombogenicity particularly under severe conditions prone to thrombus formation.

The present inventors have conducted extensive research to address the above problems. For example, they have found that the problems can be addressed by a medical device including a coating layer made of an antithrombogenic material containing a copolymer having specific repeating units, in which the content ratios of the specific repeating units are within specific ranges.

Exemplary aspects of the present disclosure are as follows.

1. A medical device including:

a base member; and a coating layer containing an antithrombogenic material and covering a surface of the base member, the antithrombogenic material containing a copolymer having:

a repeating unit (A) represented by the following formula (1):

[Chemical Formula 1]

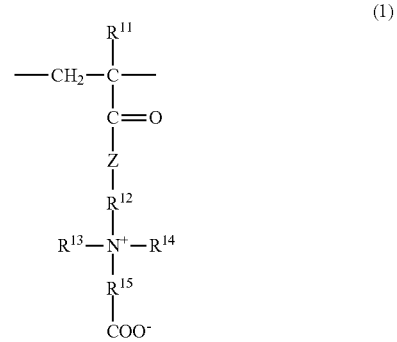

wherein $R^{11}$ is a hydrogen atom or a methyl group, Z is an oxygen atom or —NH—, $R^{12}$ is a $C_{1-6}$ alkylene group, $R^{13}$ and $R^{14}$ are each independently a $C_{1-4}$ alkyl group, and $R^{15}$ is a $C_{1-2}$ alkylene group; and a repeating unit (B) represented by the following formula (2):

[Chemical Formula 2]

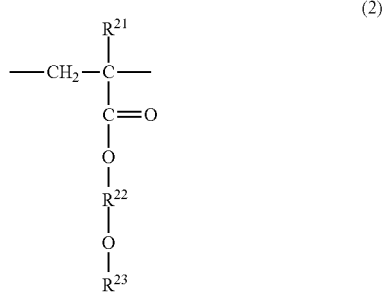

wherein $R^{21}$ is a hydrogen atom or a methyl group, $R^{22}$ is a $C_{1-6}$ alkylene group, and $R^{23}$ is a $C_{1-4}$ alkyl group, the repeating unit (A) being contained in a proportion of 1 to 7 mol % based on all the structural units of the copolymer.

2. The medical device according to 1 above, wherein in the formula (2), $R^{21}$ is a hydrogen atom or a methyl group, $R^{22}$ is a $C_{1-3}$ alkylene group, and $R^{23}$ is a $C_{1-2}$ alkyl group.

3. The medical device according to 1 or 2 above, wherein in the formula (1), $R^{11}$ is a methyl group, Z is an oxygen atom, $R^{12}$ is a $C_{1-3}$ alkylene group, and $R^{13}$ and $R^{14}$ are each independently a $C_{1-2}$ alkyl group.

4. The medical device according to any one of 1 to 3 above, wherein the copolymer includes 1 to 7 mol % the repeating unit (A) and 99 to 93 mol % the repeating unit (B) (the total amount of the repeating unit (A) and the repeating unit (B) is 100 mol %).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In FIG. 1, the circled portions each show the joint between tubes 1 and 2.

DETAILED DESCRIPTION

Figure 1:
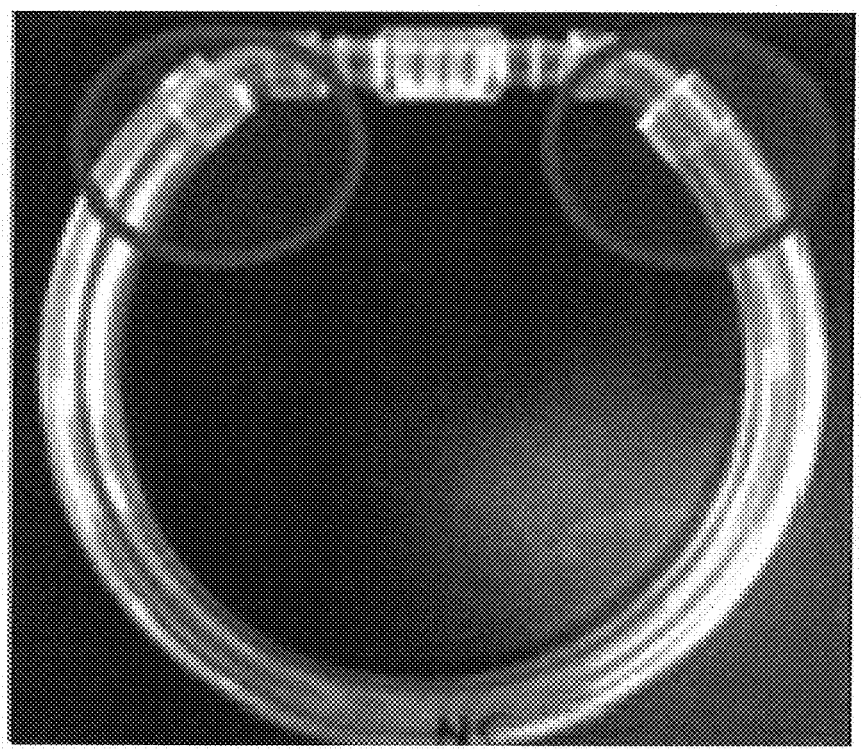
FIG. 1 shows a tube (stepped tube) used in the Examples, with both ends being connected by a connector, according to an exemplary aspect of the disclosure.

The present disclosure relates to a medical device at least partially covered with an antithrombogenic material containing a copolymer having specific repeating units.

Hereinafter, exemplary embodiments of the present disclosure will be described. The present disclosure is not limited only to the following embodiments. In addition, the scale ratio in the drawings is exaggerated for the convenience of explanation, and may be different from the actual ratio.

In addition, as used herein, "X to Y" indicating a range means "X or more and Y or less", and "weight", "wt %", and "part by weight" are treated as synonymous with "mass", "mass %", and "part by mass", respectively. In addition, unless otherwise noted, the operations, physical properties, and the like are measured under the conditions of room temperature (20 to 25° C.) and a relative humidity of 40 to 50%.

The present disclosure provides a medical device including:

a base member; and a coating layer containing an antithrombogenic material and covering a surface of the base member, the antithrombogenic material containing a copolymer having:

a repeating unit (A) represented by the following formula (1):

[Chemical Formula 3]

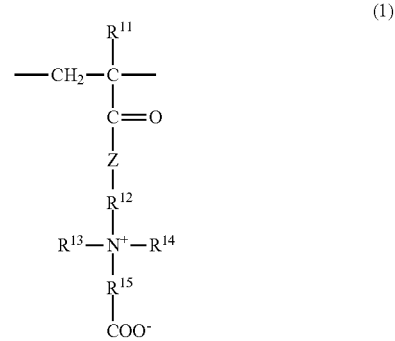

wherein $R^{11}$ is a hydrogen atom or a methyl group, Z is an oxygen atom or —NH—, $R^{12}$ is a $C_{1-6}$ alkylene group, $R^{13}$ and $R^{14}$ are each independently a $C_{1-4}$ alkyl group, and $R^{15}$ is a $C_{1-2}$ alkylene group; and a repeating unit (B) represented by the following formula (2):

[Chemical Formula 4]

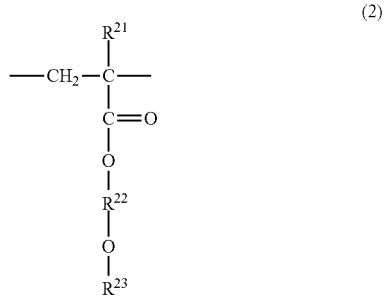

(2)

wherein $R^{21}$ is a hydrogen atom or a methyl group, $R^{22}$ is a $C_{1-6}$ alkylene group, and $R_{23}$ is a $C_{1-4}$ alkyl group,
the repeating unit (A) being contained in a proportion of 1 to 7 mol % based on all the structural units.

Hereinafter, the coating layer (antithrombogenic material to form the coating layer), which is an exemplary element of the present disclosure, will be described in detail.

[Coating Layer]

In the medical device according to an exemplary aspect, the coating layer is a layer that at least partially covers the surface of the base member and is provided to make the medical device antithrombogenic.

The antithrombogenic material forming the coating layer contains a copolymer having a repeating unit (A) represented by the above formula (1) (hereinafter also simply referred to as "repeating unit (A)") and a repeating unit (B) represented by the above formula (2) (hereinafter also simply referred to as "repeating unit (B)"), and the copolymer contains the repeating unit (A) in a proportion of 1 to 7 mol % based on all the structural units.

The present inventors have found, for example, that when the repeating unit (A) and the repeating unit (B) are combined, and a coating layer is formed using a copolymer containing these repeating units, a medical device having excellent antithrombogenicity can be obtained.

JP-A-4-152952 discloses a biocompatible biomedical material composed of a homopolymer of the repeating unit (B) or a copolymer containing the same. However, as described above, there has been a desire for further improvement in antithrombogenicity under severe conditions extremely prone to thrombus formation. For example, in order to achieve further improvement in antithrombogenicity, the present inventors have studied structural units to be contained in a copolymer together with the repeating unit (B). In the course of study, they have found that, surprisingly, when the copolymer has, as a repeating unit, a zwitterion-containing backbone such as a carboxybetaine backbone, the antithrombogenicity can be improved. While not limited to any particular theory, such improvement in antithrombogenicity appears to be attributable to the following: when a repeating unit (A) having high hydrophilicity is contained, the hydrophilicity of the copolymer is moderately controlled, and the biocompatibility is enhanced, resulting in a significantly improved inhibitory effect on thrombus formation.

For example, as a result of further study of copolymers containing the repeating units (A) and (B), it has turned out that when the content ratio of the repeating unit (A) is increased, although the antithrombogenicity is improved, the water solubility becomes too high. When a coating layer is formed using such a copolymer having extremely high water solubility, at the time of using the medical device or the like, upon contact with a body fluid such as blood, the antithrombogenic material containing the copolymer may be eluted. For example, in a blood flow circuit such as an artificial lung system, the medical device remains in contact with blood for several hours during surgery. Accordingly, in the case where the antithrombogenic material fixed to the medical device is eluted at a high rate, the antithrombogenicity of the medical device may decrease during the surgery, resulting in significant thrombus formation in the blood vessel circuit, thereby making the blood circuit unusable.

Thus, for example, the upper limit of the content ratio of the repeating unit (A) based on all the structural units of the copolymer is specified to be 7 mol %. As a result, a coating layer exhibiting excellent antithrombogenicity and also having moderately controlled water solubility can be formed.

Therefore, according to the present disclosure, a medical device having excellent antithrombogenicity, for example, under severe conditions prone to thrombus formation is provided.

The above-described mechanism is based on a theory, and the present disclosure is not limited to the above-described mechanism.

(Copolymer Contained in Antithrombogenic Material)

The copolymer contained in the antithrombogenic material according to the present disclosure is a copolymer containing the repeating units (A) and (B), in which the content ratio of the repeating unit (A) based on all the structural units is within a specific range. Therefore, as long as the copolymer has the above composition, its terminus is not particularly limited. They are suitably determined according to the kind of raw material used, and can be hydrogen atoms. The structure of the copolymer is not particularly limited either, and may be any of a random copolymer, an alternating copolymer, a periodic copolymer, and a block copolymer.

It is exemplary that the weight average molecular weight of the copolymer is 1,000 to 1,000,000. A weight average molecular weight within the above range is exemplary in terms of solubility. In terms of the ease of covering with the coating layer, it is exemplary that the weight average molecular weight of the copolymer is 50,000 to 500,000. In the present disclosure, as "weight average molecular weight", a value measured by gel permeation chromatography (GPC) using polystyrene as a reference material and tetrahydrofuran (THF) as a mobile phase is employed.

Hereinafter, each structural unit (repeating unit) of the copolymer contained in the antithrombogenic material will be described.

(I) Repeating Unit (A)

In the present disclosure, the copolymer contained in the antithrombogenic material contains a repeating unit (A) represented by the above formula (1).

In the above formula (1), $R^{11}$ is a hydrogen atom or a methyl group, and, for example, a methyl group in terms of improving the antithrombogenicity.

In the above formula (1), Z is an oxygen atom or —NH—, and, for example, an oxygen atom in terms of improving the antithrombogenicity.

In the above formula (1), $R^{12}$ is a $C_{1-6}$ linear or branched alkylene group. Specific examples thereof include a methylene group, an ethylene group, a trimethylene group, a propylene group, a tetramethylene group, a pentamethylene group, and a hexamethylene group. Among them, in terms of improving the antithrombogenicity, $C_{1-3}$ linear or branched alkylene groups are exemplary, a methylene group and an ethylene group are exemplary, and an ethylene group is exemplary.

In the above formula (1), $R^{13}$ and $R^{14}$ are each independently a $C_{1-4}$ alkyl group. Specific examples thereof include linear or branched alkyl groups such as a methyl group, an ethyl group, a propyl group, an isopropyl group, a butyl group, an isobutyl group, a sec-butyl group, and a tert-butyl group. Among them, in terms of improving the antithrombogenicity, $C_{1-3}$ linear or branched alkyl groups are exemplary, $C_{1-2}$ alkyl groups (methyl group, ethyl group) are exemplary, and a methyl group is exemplary.

In the above formula (1), $R^{15}$ is a $C_{1-2}$ linear or branched alkylene group. Specific examples thereof include a methylene group and an ethylene group. Among them, in terms of improving the antithrombogenicity, a $C^1$ alkylene group (methylene group) is exemplary.

From above, in the above formula (1) representing the repeating unit (A), it is exemplary that $R^{11}$ is a methyl group, Z is an oxygen atom, $R^{12}$ is a $C_{1-3}$ alkylene group, and $R^{13}$ and $R^{14}$ are each independently a $C_{1-2}$ alkyl group. Further, in the above formula (1), it is exemplary that $R^{11}$ is a methyl group, Z is an oxygen atom, $R^{12}$ is a $C_2$ alkylene group, and $R^{13}$ and $R^{14}$ are each independently a $C_1$ alkyl group.

The copolymer contained in the antithrombogenic material in the present disclosure can be obtained by a polymerization reaction between a monomer that forms the repeating unit (A) described above (hereinafter also referred to as "monomer a") and a monomer that forms the repeating unit (B) described below in detail (hereinafter also referred to as "monomer b").

Examples of monomers a include N-(meth)acryloyloxymethyl-N,N-dimethylammonium-α-N-methylcarboxybetaine, N-(meth)acryloyloxyethyl-N,N-dimethylammonium-α-N-methylcarboxybetaine, N-(meth)acryloyloxypropyl-N,N-dimethylammonium-α-N-methylcarboxybetaine, N-(meth)acryloyloxymethyl-N,N-diethylammonium-α-N-methylcarboxybetaine, N-(meth)acryloyloxyethyl-N,N-diethylammonium-α-N-methylcarboxybetaine, and N-(meth)acryloyloxypropyl-N,N-diethylammonium-α-N-methylcarboxybetaine. N-(meth)acryloyloxyethyl-N,N-dimethylammonium-α-N-methylcarboxybetaine (CBA) is exemplary. The above monomers may be used alone or as a mixture of two or more kinds. By using such a monomer having a betaine backbone, the coating layer of the medical device can be made highly antithrombogenic. As used herein, "(meth)acryl" means "acryl" and/or "methacryl", and "(meth)acryloyl" means "acryloyl" and/or "methacryloyl".

(II) Repeating Unit (B)

In the present disclosure, the copolymer contained in the antithrombogenic material contains a repeating unit (B) represented by the above formula (2).

In the above formula (2), $R^{21}$ is a hydrogen atom or a methyl group, and, for example, a hydrogen atom in terms of improving the antithrombogenicity.

In the above formula (2), $R^{22}$ is a $C_{1-6}$ linear or branched alkylene group. Specific examples thereof include a methylene group, an ethylene group, a trimethylene group, a propylene group, a tetramethylene group, a pentamethylene group, and a hexamethylene group. Among them, in terms of improving the antithrombogenicity, $C_{1-3}$ linear or branched alkylene groups are exemplary, a methylene group and an ethylene group are exemplary, and an ethylene group is exemplary.

In the above formula (2), $R^{23}$ is a $C_{1-4}$ linear or branched alkyl group. Specific examples thereof include linear or branched alkyl groups such as a methyl group, an ethyl group, a propyl group, an isopropyl group, a butyl group, an isobutyl group, a sec-butyl group, and a tert-butyl group. Among them, in terms of improving the antithrombogenicity, $C_{1-3}$ linear or branched alkyl groups are exemplary, $C_{1-2}$ alkyl groups (methyl group, ethyl group) are exemplary, and a methyl group is exemplary.

From above, in the above formula (2) representing the repeating unit (B), it is exemplary that $R^{21}$ is a hydrogen atom or a methyl group, $R^{22}$ is a $C_{1-3}$ alkylene group, and $R^{23}$ is a $C_{1-2}$ alkyl group. Further, in the above formula (2), it is exemplary that $R^{21}$ is a hydrogen atom or a methyl group, $R^{22}$ is a $C_2$ alkylene group, and $R^{23}$ is a $C_1$ alkyl group.

Examples of monomers b to form the repeating unit (B) include methoxymethyl acrylate, methoxyethyl acrylate (MEA), methoxypropyl acrylate, methoxybutyl acrylate, ethoxymethyl acrylate, ethoxyethyl acrylate, ethoxypropyl acrylate, ethoxybutyl acrylate, propoxymethyl acrylate, propoxyethyl acrylate, propoxypropyl acrylate, propoxybutyl acrylate, butoxymethyl acrylate, butoxyethyl acrylate, butoxypropyl acrylate, butoxybutyl acrylate, methoxymethyl methacrylate, methoxyethyl methacrylate, methoxypropyl methacrylate, methoxybutyl methacrylate, ethoxymethyl methacrylate, ethoxyethyl methacrylate, ethoxypropyl methacrylate, ethoxybutyl methacrylate, propoxymethyl methacrylate, propoxyethyl methacrylate, propoxypropyl methacrylate, propoxybutyl methacrylate, butoxymethyl methacrylate, butoxyethyl methacrylate, butoxypropyl methacrylate, and butoxybutyl methacrylate. Examples of monomers b include methoxymethyl acrylate, methoxyethyl acrylate (MEA), ethoxymethyl acrylate, ethoxyethyl acrylate, methoxymethyl methacrylate, methoxyethyl methacrylate, ethoxymethyl methacrylate, and ethoxyethyl methacrylate. In terms of availability, methoxyethyl acrylate (MEA) is exemplary. The above monomers may be used alone or as a mixture of two or more kinds.

(III) Content Ratio of Each Repeating Unit

In the present disclosure, the copolymer contains the repeating unit (A) in a proportion of, for example, 1 to 7 mol % based on all the structural units (100 mol %) of the copolymer. The repeating unit (A) is highly hydrophilic. Therefore, in the case where a large amount of repeating unit (A) is contained in the copolymer, such a copolymer exhibits excellent antithrombogenicity. Meanwhile, when the amount of repeating unit (A) is too large, the copolymer has increased water solubility. When such an antithrombogenic material is applied to a medical device, the antithrombogenic material may be released.

For example, when the repeating unit (A) is present in a proportion of less than 1 mol % based on all the structural units of the copolymer, the antithrombogenicity-improving effect cannot be sufficiently obtained, resulting in thrombus formation in severe environments, such as when used for a long period of time under conditions prone to thrombus formation. Meanwhile, when the repeating unit (A) is present in a proportion of more than 7 mol %, because of the action of the repeating unit (A) to impart water solubility, upon contact with a body fluid (e.g., blood), the antithrombogenic material covering the medical device may be released from the base member and eluted into the body fluid (contamination).

In terms of improving the antithrombogenicity and preventing the release of the antithrombogenic material at the same time, a proportion of the repeating unit (A) based on all the structural units is, for example, 2 to 6 mol %, for example, 3 to 5 mol %.

In the copolymer contained in the antithrombogenic material, as long as the repeating unit (A) based on all the structural units is within the above range, for example, the content ratio of the repeating unit (B) is not particularly limited. It is exemplary that the repeating unit (B) is contained, for example, in a proportion of 60 mol % or more based on all the structural units of the copolymer, for example, in a proportion of 80 mol % or more, and, for example, in a proportion of 90 mol % or more. Meanwhile, in relation to the repeating unit (A), the upper limit thereof is, for example, 99 mol %.

The copolymer contained in the antithrombogenic material may contain other structural units aside from the repeating units (A) and (B), but is, in an exemplary embodiment, composed only of the repeating units (A) and (B). That is, in the copolymer contained in the antithrombogenic material, it is exemplary that the total amount of the repeating unit (A) and the repeating unit (B) is 100 mol %, with respect to the copolymer.

It is exemplary that the copolymer includes 1 to 7 mol % of the repeating unit (A) and 99 to 93 mol % of the repeating unit (B) (the total amount of the repeating unit (A) and the repeating unit (B) is 100 mol %). For example, when the copolymer has the above composition, such a copolymer exhibits high antithrombogenicity even under severe conditions prone to thrombus formation. At the same time, the release of the antithrombogenic material covering the medical device from the base member and elution into a body fluid (contamination) can be reduced or prevented.

Further, it is exemplary that the copolymer contained in the antithrombogenic material includes 2 to 6 mol % of the repeating unit (A) and 98 to 94 mol % of the repeating unit (B) (the total amount of the repeating unit (A) and the repeating unit (B) is 100 mol %). Further, it is exemplary that the copolymer includes 3 to 5 mol % of the repeating unit (A) and 97 to 95 mol % of the repeating unit (B) (the total amount of the repeating unit (A) and the repeating unit (B) is 100 mol %).

As the proportions of the repeating unit (A), the repeating unit (B), and repeating units derived from other monomers in the copolymer, values determined by NMR spectroscopy are employed. For example, in the case of a copolymer composed of the repeating unit (A) and the repeating unit (B), $^1$H-NMR integration values of the alkylene group (i.e., $R^{15}$) and alkoxy group (i.e., $-OR^{23}$) on the nitrogen atom, which are characteristic structures of the repeating units (A) and (B), respectively, are determined, and, based on the ratio between the integration values, the proportions of the repeating unit (A) and the repeating unit (B) in the copolymer can be analyzed. In addition, in the case where the peaks overlap in the $^1$H-NMR measurement, $^{13}$C-NMR may be used for calculation.

(IV) Other Structural Units

As described above, the copolymer contained in the antithrombogenic material according to the present disclosure can be composed only of the repeating units (A) and (B), but may also contain other repeating units. For example, in another exemplary embodiment, the copolymer contained in the antithrombogenic material may contain structural units (repeating units) derived from the monomer a, the monomer b, and other monomers copolymerizable therewith (hereinafter also simply referred to as "other monomers").

Examples of other monomers copolymerizable with the monomer a and the monomer b include acrylamide, N,N-dimethylacrylamide, N,N-diethylacrylamide, aminomethyl acrylate, aminoethyl acrylate, aminoisopropyl acrylate, diaminomethyl acrylate, diaminoethyl acrylate, diaminobutyl acrylate, methacrylamide, N,N-dimethylmethacrylamide, N,N-diethylmethacrylamide, aminomethyl methacrylate, aminoethyl methacrylate, diaminomethyl methacrylate, diaminoethyl methacrylate, methyl acrylate, ethyl acrylate, isopropyl acrylate, butyl acrylate, 2-ethylhexyl acrylate, methyl methacrylate, ethyl methacrylate, butyl methacrylate, hexyl acrylate, hexyl methacrylate, ethylene, propylene, N-vinylacetamide, and N-isopropenylacetamide.

The proportion of repeating units derived from the above other monomers based on all the structural units of the copolymer is not particularly limited, and is, for example, more than 0 mol % and less than 39 mol %, for example, more than 0 mol % and less than 33 mol %, for example, more than 0 mol % and less than 9 mol %, and, for example, more than 0 mol % and less than 3 mol %.

(Method for Producing Copolymer)

The proportions of the repeating unit (A), the repeating unit (B), and repeating units derived from other monomers in the copolymer can be arbitrarily adjusted by changing the proportions of monomers used for polymerization. For example, at the time of polymerization, the monomer a for forming the repeating unit (A) is added in a proportion of 1 to 7 mol % based on the total number of moles of all the monomers used. Further, at this time, it is exemplary that the monomer b for forming the repeating unit (B) is added in a proportion of 99 to 93 mol % based on the total number of moles of all the monomers used. Basically, with respect to a copolymer obtained by the copolymerization of the monomer a, the monomer b, and optionally added other monomers, in the case where molecular weight fractionation or the like is not performed, the feeding ratios of the monomers used for copolymerization are equivalent to the content ratios of the corresponding repeating units in the obtained copolymer.

The method for producing the copolymer contained in the antithrombogenic material according to the present disclosure is not particularly limited. For example, known polymerization methods, such as radical polymerization, anionic polymerization, and cationic polymerization, may be employed, and it is exemplary to use radical polymerization that facilitates production. As a method for producing the copolymer contained in the antithrombogenic material according to the present disclosure, it is also possible to employ plasma polymerization by radiation or UV light, for example, thereby forming a coating layer containing the copolymer on the surface of the base member.

In an exemplary method for polymerizing the monomers, at least one kind of monomer a corresponding to the repeating unit (A) (e.g., N-methacryloyloxyethyl-N,N-dimethylammonium-α-N-methylcarboxybetaine (CBA)), at least one kind of monomer b corresponding to the repeating unit (B) (e.g., methoxyethyl acrylate (MEA)), and other monomers as desired are stirred and heated in a polymerization solvent together with a polymerization initiator, thereby causing copolymerization.

In terms of controlling the molecular weight, it is exemplary that the polymerization temperature is 30° C. to 100° C. The polymerization reaction can be carried out for 30 minutes to 24 hours.

Examples of polymerization solvents include aqueous solvents including water; alcohols such as methanol, ethanol, propanol, and n-butanol; polyalcohols such as ethylene glycol, diethylene glycol, propylene glycol, and dipropylene glycol; and the like. Methanol, ethanol, and propanol are exemplary. They may be used alone, and it is also possible to use two or more kinds together.

The monomer concentration (solids concentration) in the polymerization solvent can be 10 to 90 wt %, for example, 15 to 80 wt %, based on the entire reaction solution. The monomer concentration relative to the polymerization solvent refers to the concentration of the total weight of the monomer a, the monomer b, and optionally contained other monomers copolymerizable therewith (hereinafter "the monomer a, the monomer b, and optionally contained other monomers copolymerizable therewith" is also referred to as "polymerization monomers").

The polymerization solvent having added thereto the polymerization monomers may be subjected to a degassing treatment before the addition of a polymerization initiator. The degassing treatment may be such that, for example, the polymerization solvent having added thereto the polymerization monomers is bubbled with an inert gas, such as nitrogen gas or argon gas, for about 0.5 to 5 hours. At the time of the degassing treatment, the polymerization solvent having added thereto the polymerization monomers may be heated to about 30° C. to 100° C.

For the production of the copolymer, known polymerization initiators may be used without particular limitation. For example, azo polymerization initiators such as 2,2'-azobisisobutyronitrile, 2,2'-azobis(4-methoxy-2,4-dimethylvaleronitrile), and 2,2'-azobis(2,4-dimethylvaleronitrile); and redox polymerization initiators obtained by combining an oxidizing agent, such as persulfates such as potassium peroxodisulfate (KPS), sodium persulfate, and ammonium persulfate, or peroxides such as hydrogen peroxide, t-butyl peroxide, and methyl ethyl ketone peroxide, with a reducing agent, such as sodium sulfite, sodium hydrogensulfite, or ascorbic acid, can be used.

The amount of polymerization initiator incorporated is, for example, 0.0001 to 1 mol per mole of all the monomers used for production of a copolymer.

Further, as desired, chain transfer agents, polymerization rate regulators, surfactants, and other additives may also be suitably used for polymerization.

The atmosphere in which the polymerization reaction is carried out is not particularly limited, and the reaction may be carried out in ambient atmosphere, an inert gas atmosphere such as nitrogen gas or argon gas, or the like. In addition, the reaction mixture may be stirred during the polymerization reaction.

The copolymer after polymerization may be purified by a general purification method, such as reprecipitation, dialysis, ultrafiltration, or extraction.

The copolymer after purification may be dried by any method, such as freeze drying, vacuum drying, spray drying, or drying by heating. In terms of not significantly affecting the physical properties of the polymer, freeze drying or vacuum drying is exemplary.

(Other Components)

The antithrombogenic material according to the present disclosure may contain other components aside from the copolymer. Examples of other components include unreacted monomers that have not reacted in polymerization, as well as various additives such as crosslinking agents, thickeners, preservatives, and pH adjusters.

It is exemplary that the content of unreacted polymerization monomers in the obtained copolymer is 0.01 wt % or less based on the entire copolymer. A lower content of unreacted polymerization monomers, for example, can be desirable. Thus, the lower limit is not particularly set, but is, for example, 0 wt %. The content of residual monomers can be measured by a method known to those skilled in the art, such as high-speed liquid chromatography.

The antithrombogenic material of the present disclosure may be used in the form of the obtained copolymer, and may also be processed into a gel, a solution, or the like before use. For example, the antithrombogenic material may be used in the form of a coating agent prepared by dissolving the copolymer in a solvent.

In the case of use in the form of a coating agent, the solvent to be used is not particularly limited as long as it is capable of dissolving the copolymer. Examples thereof include alcohol solvents such as methanol, ethanol, isopropanol, and butanol, water, and non-proton-donating organic solvents such as chloroform, tetrahydrofuran, acetone, dioxane, and benzene. The above solvents may be used alone or as a mixture of two or more kinds. As a mixed solvent, a water-alcohol solvent is exemplary, and a water-methanol mixed solvent is exemplary.

The amount of copolymer contained in the coating agent may be arbitrarily set, and it is also possible to use a solution prepared by dissolving the copolymer to saturation. However, the amount is, for example, 0.1 to 50 wt % based on the entire coating agent.

The coating agent may be composed of the copolymer and the solvent, and may also optionally contain other components such as crosslinking agents, thickeners, preservatives, and pH adjusters. When a crosslinking agent is contained, the copolymer can be more firmly fixed to the surface of the base member. For example, the repeating unit (A) contained in the antithrombogenic material according to the present disclosure can be highly reactive with a crosslinking agent, and thus the antithrombogenic material can be more firmly fixed to the surface of the base member.

[Base Member]

In an exemplary medical device of the present disclosure, the surface of the base member is at least partially covered with the above antithrombogenic material. Materials that can be used for the base member are not particularly limited, and examples thereof include various polymer materials including polyolefins, such as polyethylene, polypropylene, and ethylene-α-olefin copolymers, and modified polyolefins; polyamide; polyimide; polyurethane; polyesters such as polyethylene terephthalate (PET), polybutylene terephthalate (PBT), polycyclohexane terephthalate, and polyethylene-2,6-naphthalate; polyvinyl chloride; polyvinylidene chloride (PVDC); polycarbonate; fluororesins such as polytetrafluoroethylene (PTFE) and ethylene-tetrafluoroethylene copolymers (ETFE); and the like, as well as metals such as stainless used steel (SUS), ceramic, carbon, and composite materials thereof.

The shape of the base member is not limited and is suitably selected according to the intended use of the medical device or the like. The base member may be in the shape of, for example, a tube, a sheet, a rod, or the like. The form of the base member is not limited to a molded article made of the above material alone, and the base member may also be used in the form of a blended molded article, an alloyed molded article, a multilayered molded article, or the like. The base member may have a monolayer or laminated structure. In the case of a laminated base member, the base members of the layers may be the same or different from each other. For example, in the case where it is desired to swell the base member with a solvent to firmly fix the copolymer, at least as a material present on the surface of the base member, a material that can be swollen well with the solvent of the coating agent of the antithrombogenic material is exemplary.

In the present disclosure, "a surface of a base member" is a surface of the base member that faces a biological tissue or a body fluid such as blood. When the copolymer-containing coating layer is formed on the surface of the base member, the antithrombogenicity of the surface of the base member is improved. In the medical device according to the present disclosure, for example, it is desirable that the copolymer-containing coating layer is formed on a side of the base member that faces a biological tissue or a body fluid such as blood. For example, the coating layer also can be formed on other sides.

In order to enhance the stability of the coating layer on the surface of the base member, the base member may be surface-treated before forming the coating layer on the surface of the base member. Examples of methods for surface-treating the base member include a method that applies active energy rays (electron beam, UV, X-ray, etc.), a method that utilizes plasma discharge such as arc discharge, corona discharge, or glow discharge, a method that applies a high electric field, a method that allows ultrasonic vibration through a polar liquid (water, etc.) to act, and a method of treating the surface with ozone gas.

[Method for Forming Coating Layer]

In an exemplary medical device according to the present disclosure, the surface of the base member is at least partially covered with the antithrombogenic material to form a coating layer.

The formation of a coating layer on the surface of the base member may be performed by applying a coating liquid containing the antithrombogenic material (e.g., the above coating agent), thereby covering the surface of the base member, or by applying a polymerization solvent containing polymerization monomers for obtaining the copolymer to the surface of the base member, followed by plasma polymerization. In terms of the ease of production, it is exemplary that the coating layer is formed by covering the surface of the base member with a coating liquid containing the antithrombogenic material. For example, "covering" includes not only an exemplary embodiment in which the entire surface of the base member is completely covered with the coating layer, but also an exemplary embodiment in which the surface of the base member is partially covered with the coating layer, that is, an exemplary embodiment in which the coating layer is attached to a part of the surface of the base member.

In an exemplary embodiment where the coating layer is formed by covering the surface of the base member with a coating liquid containing the antithrombogenic material, for the method for preparing a coating liquid containing the antithrombogenic material, the method for preparing a coating agent described above can be adapted for use.

As the method for applying a coating liquid containing the antithrombogenic material to the surface of the base member, known methods may be employed without particular limitation. Examples thereof include dip coating, spraying, spin coating, dripping, doctor blading, brush coating, roll coating, air knife coating, curtain coating, wire bar coating, and gravure coating.

The thickness of the coating liquid (coating layer) may be suitably adjusted according to the intended use of the medical device and is not particularly limited, and is, for example, 0.1 μm to 1 mm.

For example, by drying the surface of the base member having applied thereto the copolymer-containing coating liquid, a coating layer is formed on the surface of the base member. The drying step may be suitably selected considering the glass transition temperature of the base member or the like, and is, for example, 15° C. to 50° C. The atmosphere during the drying step is not particularly limited, and the step may be performed in ambient atmosphere or an inert gas atmosphere such as nitrogen gas or argon gas.

[Examples of Medical Devices]

Examples of medical devices according to the present disclosure include implantable prostheses and treating instruments, artificial organs for extracorporeal circulation, catheters, and guidewires. Specific examples thereof include artificial blood vessels, artificial tracheas, and stents inserted into, or to replace, blood vessels or lumens; implantable medical instruments such as artificial skins and artificial pericardia; artificial organ systems such as artificial heart systems, artificial lung systems, artificial heart-lung systems, artificial kidney systems, artificial liver systems, and immunoregulation systems; catheters inserted into or indwelled in blood vessels, such as indwelling needles, IVH catheters, catheters for liquid medicine administration, thermodilution catheters, angiographic catheters, vasodilatation catheters, dilators, and introducers, as well as guidewires, stylets, and the like for these catheters; various suction catheters such as stomach tube catheters, nutrition catheters, feeding (ED) tubes, urethral catheters, urine drainage catheters, balloon catheters, and tracheal suction catheters; and catheters inserted into or indwelled in biological tissues other than blood vessels, such as drainage catheters. For example, an artificial lung system, for example, is used continuously for a long period of time and also has several steps at tube connections and the like. For example, the present disclosure is suitable for use as an artificial lung system or an artificial heart-lung system, which contacts a large amount of blood.

EXAMPLES

Exemplary effects of the present disclosure will be described hereinafter through examples and comparative examples. However, the technical scope of the present disclosure is not limited only to the following examples.

Example 1

Copolymer of CBA and MEA (Repeating Unit (A): 1.78 Mol %)

5 g (38.4 mmol) of methoxyethyl acrylate (MEA) and 0.15 g (0.70 mmol) of N-methacryloyloxyethyl-N,N-dimethylammonium-α-N-methylcarboxybetaine (CBA, a compound of the following chemical formula (i)) were dissolved in 25.5 g of methanol, placed in a four-necked flask, and bubbled with $N_2$ at 50° C. for 1 hour.

[Chemical Formula 5]

[Chemical Formula (i)]

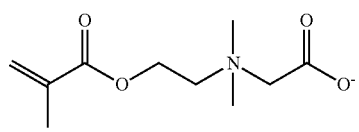

Subsequently, a solution prepared by dissolving 0.006 g of 2,2'-azobis(4-methoxy-2,4-dimethylvaleronitrile) (V-70, manufactured by Wako Pure Chemical Industries) in 1 mL of methanol was added to the methanol solution having dissolved therein the polymerization monomers, followed by polymerization at 50° C. for 5 hours. The polymerization liquid was added dropwise to diethyl ether, and the precipitated copolymer was recovered to give a polymer (1). The content ratio of the repeating unit (A) in the polymer (1) was measured by $^1$H-NMR. As a result, the ratio was the same as the value calculated from the above feeding amount. In addition, the content ratio of the repeating unit (B) was also the same as the value calculated from the feeding amount (98.22 mol %).

Example 2

Copolymer of CBA and MEA (Repeating Unit (A): 3.50 Mol %)

A polymer (2) was obtained in the same manner as in Example 1, except that the amount of CBA used in the preparation of the copolymer in Example 1 was changed to 0.3 g (1.39 mmol). The content ratio of the repeating unit (A) in the polymer (2) was measured by $^1$H-NMR. As a result, the ratio was the same as the value calculated from the above feeding amount. In addition, the content ratio of the repeating unit (B) was also the same as the value calculated from the feeding amount (96.50 mol %).

Example 3

Copolymer of CBA and MEA (Repeating Unit (A): 5.16 Mol %)

A polymer (3) was obtained in the same manner as in Example 1, except that the amount of CBA used in the preparation of the copolymer in Example 1 was changed to 0.45 g (2.09 mmol). The content ratio of the repeating unit (A) in the polymer (3) was measured by $^1$H-NMR. As a result, the ratio was the same as the value calculated from the above feeding amount. In addition, the content ratio of the repeating unit (B) was also the same as the value calculated from the feeding amount (94.84 mol %).

Comparative Example 1

Copolymer of CBA and MEA (Repeating Unit (A): 8.82 Mol %)

A comparative polymer (1) was obtained in the same manner as in Example 1, except that the amount of CBA used in the preparation of the copolymer in Example 1 was changed to 0.8 g (3.72 mmol). The content ratio of the repeating unit (A) in the comparative polymer (1) was measured by $^1$H-NMR. As a result, the ratio was the same as the value calculated from the above feeding amount. In addition, the content ratio of the repeating unit (B) was also the same as the value calculated from the feeding amount (91.18 mol %).

Comparative Example 2

Copolymer of CBA and MEA (Repeating Unit (A): 0.84 Mol %)

A comparative polymer (2) was obtained in the same manner as in Example 1, except that the amount of CBA used in the preparation of the copolymer in Example 1 was changed to 0.07 g (0.33 mmol). The content ratio of the repeating unit (A) in the comparative polymer (2) was measured by $^1$H-NMR. As a result, the ratio was the same as the value calculated from the above feeding amount. In addition, the content ratio of the repeating unit (B) was also the same as the value calculated from the feeding amount (99.16 mol %).

Comparative Example 3

Copolymer of CBA and HMA (Repeating Unit (A): 32.18 Mol %)

A comparative polymer (3) was obtained in the same manner as in Example 1, except that MEA used in the preparation of the copolymer in Example 1 was replaced with 4 g (23.49 mmol) of hexyl methacrylate (HMA), and the amount of CBA was changed to 2.4 g (11.15 mmol). The content ratio of the repeating unit (A) in the comparative polymer (3) was measured by $^1$H-NMR. As a result, the ratio was the same as the value calculated from the above feeding amount. In addition, the content ratio of the repeating unit derived from HMA was also the same as the value calculated from the feeding amount (67.82 mol %).

Comparative Example 4

Copolymer of CBA and BMA (Repeating Unit (A): 35.08 Mol %)

A comparative polymer (4) was obtained in the same manner as in Example 1, except that MEA used in the preparation of the copolymer was replaced with 5.5 g (38.68 mmol) of butyl methacrylate (BMA), the amount of CBA was changed to 4.5 g (20.90 mmol), and they were dissolved in 50 g of methanol. The content ratio of the repeating unit (A) in the polymer (4) was measured by $^1$H-NMR. As a result, the ratio was the same as the value calculated from the above feeding amount. In addition, the content ratio of the repeating unit derived from BMA was also the same as the value calculated from the feeding amount (64.92 mol %).

Comparative Example 5

(Homo)polymer of MEA (Repeating Unit (A): 0 Mol %)

A comparative polymer (5) was obtained in the same manner as in Example 1, except that 5 g (38.4 mmol) of MEA in the preparation of the copolymer in Example 1 was used alone. That is, the comparative polymer (5) was obtained as a homopolymer of MEA. In addition, the weight average molecular weight of the comparative polymer (5) was 130,000. The weight average molecular weight was measured by GPC as described above.

The polymers (1) to (3) and comparative polymers (1) to (5) obtained in the examples and comparative examples were purified by reprecipitation in diethyl ether. Subsequently, these copolymers or polymers were dried by vacuum drying and subjected to the following tests.

Test Example 1

Polymer (Copolymer or Polymer) Solubility Test 0.1-g samples were weighed from the polymers (1) to (3) and comparative polymer (1) obtained in the examples and comparative example, and placed in separate test tubes made of glass.

5 g of physiological saline was added to each test tube and stirred, and the solubility of the polymer was examined. As visually observed, in the case where the polymer maintained its form as placed in the glass test tube, such a polymer was considered as insoluble in water. In the case where there was no insoluble matter, or it was slightly cloudy but dispersed, such a polymer was considered to be dissolved in water.

TABLE 1

Solubility in Water

| | Solubility in Water |
|---|---|
| Example 1 (MEA-CBA copolymer, CBA: 1.78 mol %) | Insoluble |
| Example 2 (MEA-CBA copolymer, CBA: 3.50 mol %) | Insoluble |
| Example 3 (MEA-CBA copolymer, CBA: 5.16 mol %) | Insoluble |
| Comparative Example 1 (MEA-CBA copolymer, CBA: 8.82 mol %) | Dissolved |

As shown in Table 1, even in the case of a copolymer containing the repeating unit (A) having high hydrophilicity, when the proportion of the repeating unit (A) is 7 mol % or less based on all the structural units of the copolymer, such a copolymer is not dissolved in physiological saline.

This result shows that when the proportion of the repeating unit (A) is 7 mol % or less based on all the structural units of the copolymer, the base member can be suitably coated with the antithrombogenic material, and also the antithrombogenic material (coating layer) can be more effectively prevented from being released from the base member and contaminating blood.

In addition, when the proportion of the repeating unit (A) is 6 mol % or less based on all the structural units of the copolymer, the dissolution in physiological saline can be particularly inhibited. Therefore, it is suggested that when the proportion of the repeating unit (A) is 6 mol % or less based on all the structural units of the copolymer, the antithrombogenic material (coating layer) can be even more effectively prevented from being released from the base member and contaminating blood.

Test Example 2

Antithrombogenicity Test (Preparation of Coating Agent)

0.5 wt % methanol solutions of the above polymers (1) to (3) and comparative polymers (2) to (5) obtained in the examples and comparative examples were prepared and used as coating agents.

(Production of Medical Device)

At each end of a soft vinyl chloride tube 30 cm in overall length×8 mm in inner diameter (tube 1), 1 cm of an end of a soft vinyl chloride tube (tube 2) 5 cm in overall length×6 mm in inner diameter×9 mm in outer diameter was inserted, thereby producing a stepped tube.

FIG. 1 shows the produced stepped tube. In FIG. 1, the circled portions each show the joint between the tubes 1 and 2.

Figure 2:
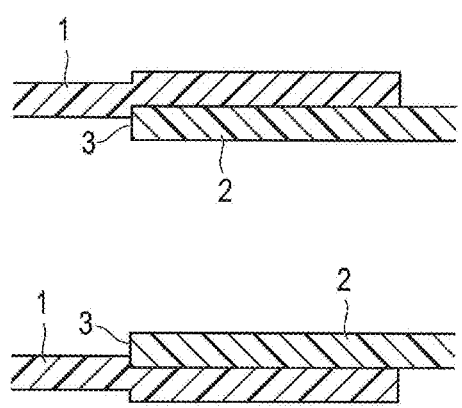
FIG. 2 is an enlarged view schematically showing a longitudinal cross-section of the joint between tubes 1 and 2 in FIG. 1, according to an exemplary aspect of the disclosure.

FIG. 2 is an enlarged view schematically showing the joint between the tubes 1 and 2 in FIG. 1. The inner diameter of the tube 2 is smaller than the inside diameter of the tube 1, and thus a stepped surface 3 is formed. In the case where blood is passed through the stepped tube, it is highly likely that thrombus formation occurs at the stepped surface 3.

Using the produced stepped tube as a base member, the above coating agent was passed through the stepped tube to apply the coating agent to the surface of the base member. Subsequently, the stepped tube was dried at room temperature (25° C.), thereby forming a coating layer containing an antithrombogenic material on the surface of the base member (the lumenal surface of the stepped tube). At this time, the (co)polymers obtained in the above examples and comparative examples were each dissolved in methanol to prepare a 0.5 wt % solution, and used for dip coating to form the coating layer.

(Antithrombogenicity Test)

In order to evaluate the antithrombogenicity of an antithrombogenic material under severe conditions prone to thrombus formation, the following test system was established using the above stepped tube having formed therein a coating layer.

That is, the lumen of the stepped tube having formed therein a coating layer was filled with 6 ml of a liquid prepared by diluting human fresh blood 2-fold with physiological saline (diluted blood). Both ends of the stepped tube were connected with a connector, fixed to a cylindrical rotator, and rotated at 40 rpm for 2 hours. Subsequently, the circulating blood was removed from the stepped tube, and thrombus attachment (indicated by the reference numeral "4" in FIG. 4) to the joint between the tubes 1 and 2 (stepped surface) was visually observed. Here, "fresh blood" means blood collected from a healthy donor within 30 minutes of use. The fresh blood has no anticoagulant added.

Figure 3:
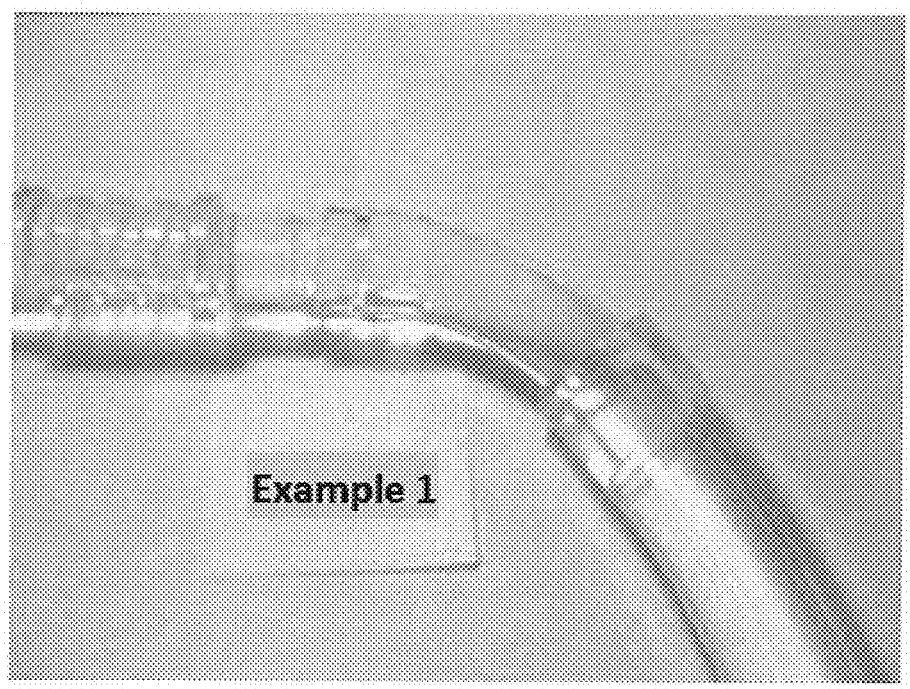
FIG. 3 is an enlarged photograph of a joint in a stepped tube having applied thereto an antithrombogenic material containing the polymer (1) produced in Example 1, immediately after the antithrombogenicity test, according to an exemplary aspect of the disclosure.
Figure 4:
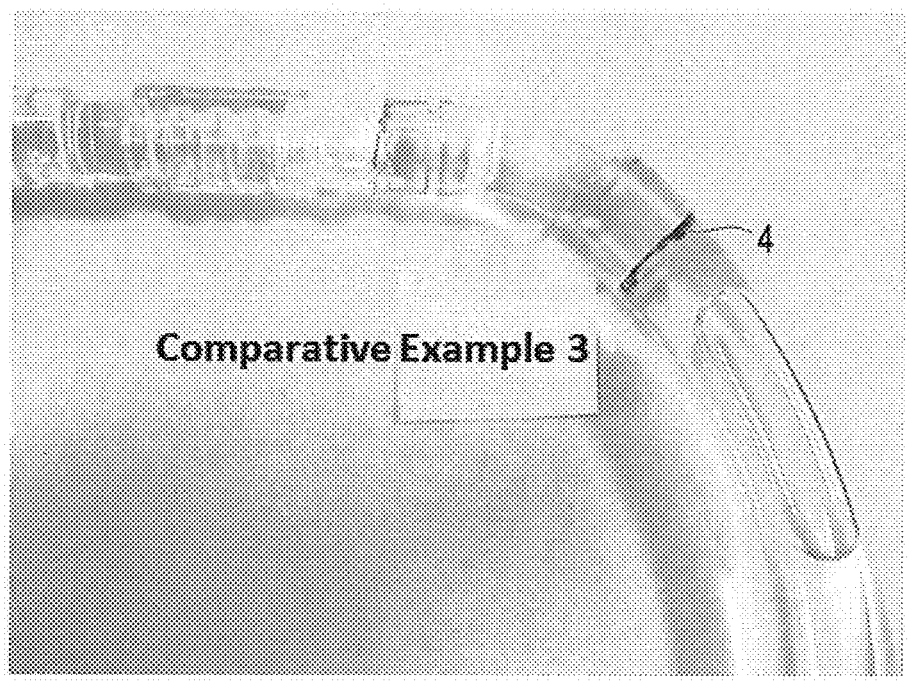
FIG. 4 is an enlarged photograph of a joint in a stepped tube having applied thereto an antithrombogenic material containing the comparative polymer (3) produced in Comparative Example 3, immediately after the antithrombogenicity test, according to an exemplary aspect of the disclosure.

FIG. 3 and FIG. 4 are enlarged photographs of joints in stepped tubes having applied thereto coating layers each containing the copolymer produced in Example 1 or the polymer produced in Comparative Example 3, immediately after the antithrombogenicity test. In the stepped tube having applied thereto the copolymer according to the present disclosure, thrombus formation was not observed (FIG. 3). Meanwhile, in the stepped tube having applied thereto the polymer of Comparative Example 3, a thrombus 4 was observed at the joint (FIG. 4).

TABLE 2

Thrombus Formation at Steps

| | Thrombus Formation at Steps |
|---|---|
| Example 1 (MEA-CBA copolymer, CBA: 1.78 mol %) | Not formed |
| Example 2 (MEA-CBA copolymer, CBA: 3.50 mol %) | Not formed |
| Example 3 (MEA-CBA copolymer, CBA: 5.16 mol %) | Not formed |
| Comparative Example 2 (MEA-CBA copolymer, CBA: 0.84 mol %) | Formed |
| Comparative Example 3 (HMA-CBA copolymer, CBA: 32.18 mol %) | Formed |
| Comparative Example 4 (BMA-CBA copolymer, CBA: 35.08 mol %) | Formed |
| Comparative Example 5 (MEA homopolymer) | Formed |

As shown in Table 2, FIG. 3, and FIG. 4, the medical devices according to the present disclosure exhibited high antithrombogenicity.

For example, it can be seen that when the proportion of the repeating unit (A) is 1 mol % or more based on all the structural units of the copolymer, high antithrombogenicity can be obtained even under severe use conditions. Further, in the antithrombogenicity test, as a result of visual evaluation, it was found out that when the proportion of the repeating unit (A) was 2 to 6 mol %, particularly excellent antithrombogenicity was obtained.

In addition, even when the percentage of the repeating unit (A) in all the structural units of the copolymer was high, in the case where it was not a copolymer of the repeating unit (A) and the repeating unit (B), high antithrombogenicity was not obtained under severe use conditions.

[Test 3: Blood Circulation Test Using Simulated Product Form]

The antithrombogenicity of base members coated with the polymer (1) obtained in Example 1 and the comparative polymer (5) obtained in Comparative Example 5 was evaluated in accordance with the following method.

(Preparation of Coating Agent)

The polymer (1) and the comparative polymer (5) were each dissolved in a water-alcohol (methanol) mixed solution to a concentration of 0.2 wt % and used as a coating agent.

(Production of Medical Device)

A simulated product form (blood circulation module: the hollow fiber membrane artificial lung for external hemoperfusion according to Example 1 disclosed in JP-A-11-114056, used as an artificial lung having the structure disclosed in FIG. 4 of JP-A-2009-219936; the base member forming the blood circulation pathway includes polypropylene, polyurethane, polycarbonate, SUS) was filled with the above coating agent from the blood import side and allowed to stand for 120 seconds. The coating agent was then removed, followed by blow drying at room temperature (25° C.) for 240 minutes.

(Evaluation)

The above blood circulation module was connected to a blood reservoir using a connection tube (made of flexible polyvinyl chloride, about 100 cm in overall length×8 mm in inner diameter) and thereby incorporated into an extracorporeal circulation circuit. Subsequently, the extracorporeal circulation circuit was filled with 200 ml of Ringer's lactate, and then 200 ml of heparin-added human fresh blood was added. The heparin concentration in the circulating blood was set at 0.5 units/ml. Circulation was performed at room temperature (25° C.), 500 ml/min. After 120 minutes from the start of circulation, the blood was sampled from each blood circulation circuit, and the thrombin-antithrombin complex (TAT) concentration, which is an index of the activation of the blood coagulation system, was measured. The TAT concentration was measured using a measurement kit by EIA method. A high TAT concentration indicates an activated state of coagulation, where it can be said that thrombus formation is likely to occur.

TABLE 3

TAT Concentration

| | TAT Concentration [ng/ml] |
|---|---|
| Coated with Polymer (1) of Example 1 | 50 |
| Coated with Comparative Polymer (5) of Comparative Example 5 | 2640 |

In the blood circulation module coated with the copolymer (1) of Example 1, the TAT concentration was lower than in the blood circulation module coated with the comparative polymer (5) of Comparative Example 5. That is, it was confirmed that in the medical device according to the present disclosure, the activation of the blood coagulation system is low, indicating excellent antithrombogenicity.

Figure 5:
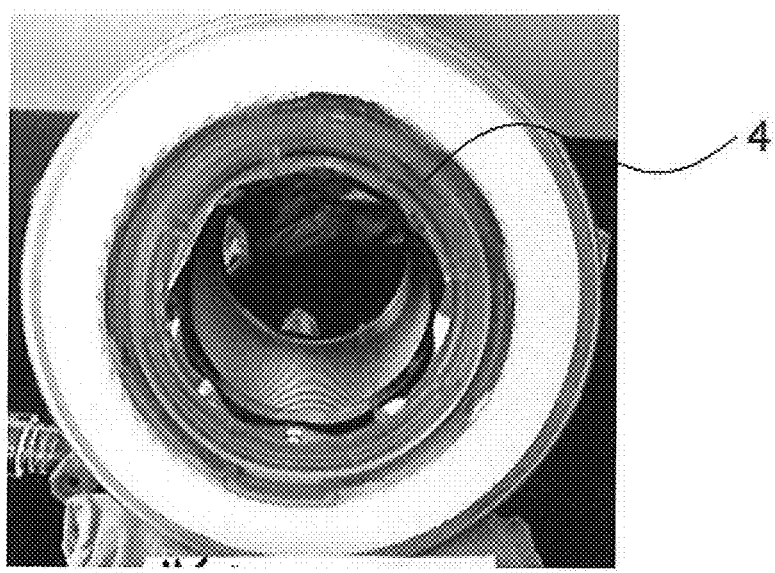
FIG. 5 is a photograph of a blood circulation module having applied thereto an antithrombogenic material containing the polymer (1) produced in Example 1, immediately after the blood circulation test, according to an exemplary aspect of the disclosure.
Figure 6:
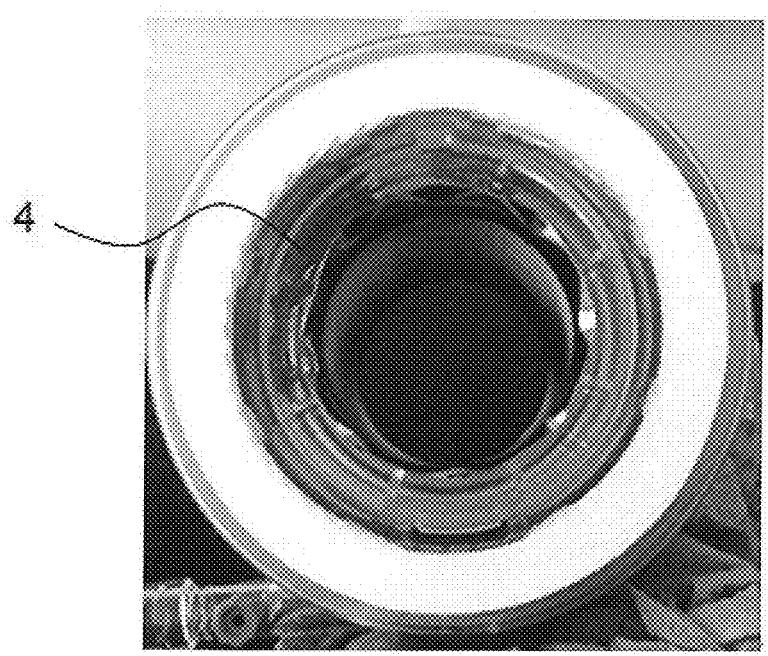
FIG. 6 is a photograph of a blood circulation module having applied thereto an antithrombogenic material containing the comparative polymer (5) produced in Comparative Example 5, immediately after the blood circulation test, according to an exemplary aspect of the disclosure.

Circulation was continued for further 6 hours, then the blood circulation pathway was washed with phosphate buffered saline (PBS), and regions where the blood was likely to be stagnant were observed. In the blood circulation module coated with the polymer (1) of Example 1, thrombus attachment (indicated by the reference numeral "4" in FIG. 5) was hardly seen. In contrast, in the blood circulation module coated with the comparative polymer (5) of Comparative Example 5, thrombus attachment (indicated by the reference numeral "4" in FIG. 6) was seen. It was confirmed that the polymer (1) of Example 1 had excellent antithrombogenicity also in a simulated product.

From above, it can be seen that the medical device according to the present disclosure exhibits excellent antithrombogenicity even when used under severe conditions prone to thrombus formation, as in the case of a medical device having a constricted portion such as a tube joint, for example, where steps are present on the surface that contacts blood.

Further, this application is based on Japanese Patent Application No. 2013-270963 filed on Dec. 27, 2013, the contents of which are entirely incorporated herein by reference.

The present invention is not limited to the precise embodiments and variations described above. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

REFERENCE NUMERAL LIST

1: Tube 1
2: Tube 2
3: Stepped surface
4: Thrombus

What is claimed is:
1. A medical device, comprising:
a base member; and
a coating layer containing an antithrombogenic material and at least partially covering a surface of the base member,
wherein the antithrombogenic material comprises a copolymer comprising:
a repeating unit (A) represented by the following formula (1):

Formula (1)

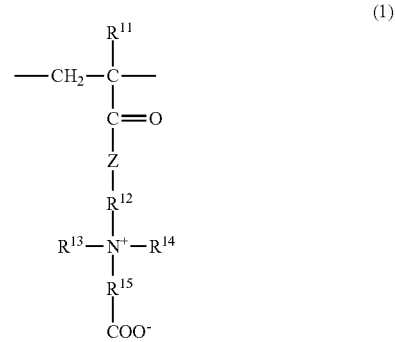

wherein $R^{11}$ is a hydrogen atom or a methyl group, Z is an oxygen atom or —NH—, $R^{12}$ is a $C_{1-6}$ alkylene group, R13 and R14 are each independently a $C_{1-4}$ alkyl group, and $R^{15}$ is a $C_{1-2}$ alkylene group; and a repeating unit (B) represented by the following formula (2):

Formula (2)

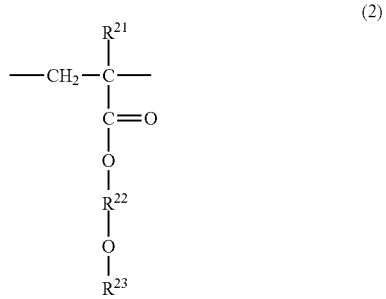

(2)

wherein $R^{21}$ is a hydrogen atom or a methyl group, $R^{22}$ is a $C_{1-6}$ alkylene group, and $R^{23}$ is a $C_{1-4}$ alkyl group, wherein the repeating unit (A) is contained in a proportion of 1 to 7 mol % based on all the structural units of the copolymer.

2. The medical device according to claim 1, wherein in the formula (2), $R^{21}$ is a hydrogen atom or a methyl group, $R^{22}$ is a $C_{1-3}$ alkylene group, and $R^{23}$ is a $C_{1-2}$ alkyl group.

3. The medical device according to claim 1, wherein in the formula (2), $R^{21}$ is a hydrogen atom, $R^{22}$ is a methylene group or an ethylene group, and $R^{23}$ is a methyl group.

4. The medical device according to claim 3, wherein in the formula (2), $R^{22}$ is an ethylene group.

5. The medical device according to claim 1, wherein in the formula (1), $R^{11}$ is a methyl group, Z is an oxygen atom, $R^{12}$ is a $C_{1-3}$ alkylene group, and $R^{13}$ and $R^{14}$ are each independently a $C_{1-2}$ alkyl group.

6. The medical device according to claim 1, wherein in the formula (1), $R^{11}$ is a methyl group, Z is an oxygen atom, $R^{12}$ is a methylene group or an ethylene group, and $R^{13}$ and $R^{14}$ are each a methyl group.

7. The medical device according to claim 6, wherein in the formula (1), $R^{15}$ is a methylene group.

8. The medical device according to claim 1, wherein in the formula (2), $R^{21}$ is a hydrogen atom or a methyl group, $R^{22}$ is a $C_{1-3}$ alkylene group, and $R^{23}$ is a $C_{1-2}$ alkyl group, and wherein in the formula (1), $R^{11}$ is a methyl group, Z is an oxygen atom, $R^{12}$ is a $C_{1-3}$ alkylene group, and $R^{13}$ and $R^{14}$ are each independently a $C_{1-2}$ alkyl group.

9. The medical device according to claim 1, wherein the copolymer includes 1 to 7 mol % of the repeating unit (A) and 99 to 93 mol % of the repeating unit (B), based on all the structural units of the copolymer.

10. The medical device according to claim 8, wherein the copolymer includes 1 to 7 mol % of the repeating unit (A) and 99 to 93 mol % of the repeating unit (B), based on all the structural units of the copolymer.

11. The medical device according to claim 1, wherein the repeating unit (A) is contained in a proportion of 2 to 6 mol %, based on all the structural units of the copolymer.

12. The medical device according to claim 1, wherein the repeating unit (A) is contained in a proportion of 3 to 5 mol %, based on all the structural units of the copolymer.

13. The medical device according to claim 1, wherein the repeating unit (B) is contained in a proportion of 60 to 99 mol %, based on all the structural units of the copolymer.

14. The medical device according to claim 1, wherein the repeating unit (B) is contained in a proportion of 90 to 99 mol %, based on all the structural units of the copolymer.

15. The medical device according to claim 1, wherein the total amount of the repeating unit (A) and the repeating unit (B) is 100 mol %, based on all the structural units of the copolymer.

16. The medical device according to claim 1, wherein the antithrombogenic material further comprises a crosslinking agent, a thickener, a preservative, or a pH adjuster.

17. The medical device according to claim 1, wherein the base member comprises a polymer material, a metal, a ceramic, carbon, or a composite material thereof.

18. The medical device according to claim 1, wherein the surface of the base member is completely covered with the coating layer.

19. The medical device according to claim 1, wherein a thickness of the coating layer is 0.1 µm to 1 mm.

20. The medical device according to claim 1, wherein the medical device is an implantable prosthesis, an implantable treating instrument, an artificial organ for extracorporeal circulation, a catheter, or a guidewire.

21. The medical device according to claim 1, wherein the repeating unit (A) is contained in a proportion of 2 to 6 mol %, based on all the structural units of the copolymer, wherein the repeating unit (B) is contained in a proportion of 90 to 98 mol %, based on all the structural units of the copolymer.

* * * * *